United States Patent
Cruz et al.

(10) Patent No.: US 6,706,282 B1
(45) Date of Patent: Mar. 16, 2004

(54) CONTROLLED DELIVERY OF PHENOXYETHYL-SUBSTITUTED 1,2,4-TRIAZOLONES

(76) Inventors: Evangeline Cruz, 3889 Blackstone Ct., Hayward, CA (US) 94542; Noymi Yam, 386 Dennis Ave., Sunnyvale, CA (US) 94086; Adam Zhong, 1206 Gingerwood Dr., Milpitas, CA (US) 95035; Atul Devdatt Ayer, 931 Bautista Ct., Palo Alto, CA (US) 94303; Padmanabh Bhatt, 18385 Vanderbilt Dr., Saratoga, CA (US) 95070

( * ) Notice: Subject to any disclaimer, the term of this patent is extended or adjusted under 35 U.S.C. 154(b) by 0 days.

(21) Appl. No.: 09/430,838

(22) Filed: Nov. 1, 1999

Related U.S. Application Data

(60) Provisional application No. 60/106,677, filed on Nov. 2, 1998.

(51) Int. Cl.[7] ................................................ A61K 9/24
(52) U.S. Cl. ...................... 424/473; 424/468; 424/472; 514/272
(58) Field of Search .................. 424/480, 458, 424/422, 484, 464, 468, 473, 472; 514/255, 252; 128/260

(56) References Cited

U.S. PATENT DOCUMENTS

| | | | |
|---|---|---|---|
| 2,799,241 A | | 7/1957 | Wurster |
| 3,133,132 A | | 5/1964 | Loeb et al. |
| 3,173,876 A | | 3/1965 | Jackson |
| 3,276,586 A | | 10/1966 | Rosean |
| 3,541,005 A | | 11/1970 | Strathmann et al. |
| 3,541,006 A | | 11/1970 | Bixler et al. |
| 3,546,142 A | | 12/1970 | Michaels et al. |
| 3,845,770 A | | 11/1974 | Theeuwes et al. |
| 3,865,108 A | | 2/1975 | Hartop |
| 3,916,899 A | * | 11/1975 | Theeuwes et al. ........... 128/260 |
| 4,002,173 A | | 1/1977 | Manning et al. |
| 4,063,064 A | | 12/1977 | Saunders et al. |
| 4,077,407 A | | 3/1978 | Theeuwes et al. |
| 4,088,864 A | | 5/1978 | Lund et al. |
| 4,160,020 A | | 7/1979 | Ayer et al. |
| 4,207,893 A | | 6/1980 | Michaels |
| 4,338,317 A | | 7/1982 | Temple, Jr. et al. |
| 4,892,778 A | | 1/1990 | Theeuwes et al. |

(List continued on next page.)

FOREIGN PATENT DOCUMENTS

| | | |
|---|---|---|
| EP | 0 966 966 A2 | 6/1999 |
| WO | Wo 97/47285 | 12/1997 |

OTHER PUBLICATIONS

Larry Hixon, et al., "Sizing Materials by Crushing and Grinding", *Chemical Engineering*, 94–103, 1990.
Eugene L. Parrott, "Milling of Pharmaceutical Solids", *Journal of Pharmaceutical Sciences*, 61(6):813–829, 1974.
*Perry's Chemical Engineers Handbook*, Perry, Green & Maloney Editors, et al, 6th Ed., "Introduction to Screening and Wet Classification", pp. 21.13 to 21.19, 1984.
*Remington's Pharmaceutical Sciences*, 17th Ed. pp. 1585–1594, 1985.
B.P. Rouse, Jr., "Cellulose Esters, Organic", *Encyclopedia of Polymer Science and Technology*, 3:325–354, 1964, (Interscience Publishers Inc., New York, NY.).
Dale E. Wurster, "Air–Suspension Technique of Coating Drug Particles", *J. Am. Pharm. Assoc.* 48(8):451–454, Aug. 1959.
Dale E. Wurster, "Preparation of Compressed Tablet Granulations by the Air–Suspension Technique ll", *J. Am. Pharm. Assoc*, 49(2):82–84, Feb. 1960.

*Primary Examiner*—Thurman K. Page
*Assistant Examiner*—Liliana Di Nola-Baron

(57) ABSTRACT

Dosage forms and methods for the controlled release of antidepressives, such as exemplified by phenoxyethyl substituted-1,2,4-triazolones, as a suspension or a slurry over a prolonged period of time are described.

26 Claims, 2 Drawing Sheets

U.S. PATENT DOCUMENTS

| | | |
|---|---|---|
| 4,915,949 A | 4/1990 | Wong et al. |
| 4,931,285 A | 6/1990 | Edgren et al. |
| 4,940,465 A | 7/1990 | Theeuwes et al. |
| 5,006,346 A | 4/1991 | Edgren et al. |
| 5,024,842 A | 6/1991 | Edgren et al. |
| 5,126,142 A | 6/1992 | Ayer et al. |
| 5,160,743 A | 11/1992 | Edgren et al. |
| 5,169,683 A | 12/1992 | Matsui et al. |
| 5,190,765 A | 3/1993 | Jao et al. |
| 5,252,338 A | 10/1993 | Jao et al. |
| 5,324,280 A * | 6/1994 | Wong et al. ............. 604/892.1 |
| 5,326,570 A * | 7/1994 | Rudnic et al. .............. 424/458 |
| 5,330,762 A | 7/1994 | Ayer et al. |
| 5,536,507 A * | 7/1996 | Abramowitz et al. ....... 424/479 |
| 5,620,705 A | 4/1997 | Dong et al. |
| 5,663,011 A | 9/1997 | Bunyea et al. |
| 6,008,222 A * | 12/1999 | Salazar ....................... 514/255 |
| 6,120,803 A * | 9/2000 | Wong et al. ................ 424/473 |

\* cited by examiner

CONTROLLED DELIVERY OF PHENOXYETHYL-SUBSTITUTED 1,2,4-TRIAZOLONES

This application claims the priority of provisional application No. 60/106,677, filed Nov. 2, 1998.

FIELD OF THE INVENTION

This invention pertains to the controlled delivery of pharmaceutical agents and methods, dosage forms and devices therefor. In particular, the invention is directed to methods, dosage forms and devices for the controlled delivery of phenoxyethyl-substituted 1,2,4-triazolones that are useful as pharmaceutical agents, such as antidepressants, for example, nefazodone and nefazodone hydrochloride.

BACKGROUND OF THE INVENTION

Phenoxyethyl substituted-1,2,4-triazolones have been described as potent antidepressants in U.S. Pat. No. 4,338,317, which is incorporated herein by reference in its entirety. One of the most effective antidepressants in that group of compounds is nefazodone hydrochloride, sold under the trademark Serzone® by Bristol-Myers Squibb Co., and having the chemical name 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride. Nefazodone hydrochloride and related compounds in the foregoing class of compounds, while rapidly absorbed, may be subject to extensive metabolism, resulting in low and variable bioavailability. For example, peak plasma concentrations for nefazodone hydrochloride occur at about one hour after dosing using conventional immediate release formulations and the half-life of nefazodone hydrochloride is on the order of 2–4 hours. The low bioavailability and short half-life of the aforementioned compounds results in the need for multiple daily dosing or dosing at drug levels that are high enough to obtain the desired anti-depressant effect, both of which may result in the occurrence of undesirable side effects in particular individuals under certain circumstances.

The art is replete with descriptions of dosage forms for the controlled release of pharmaceutical agents. For example, U.S. Pat. No. 5,536,507 describes a three component pharmaceutical formulation that utilizes, inter alia, a pH sensitive polymer and optionally an osmotic agent that will swell in the higher pH regions of the lower portion of the small intestine and the large intestine to release drug in those environments. Additional components of the dosage form include a delayed release coating and an enteric coating to provide a dosage form that releases very little, if any, of the drug in the stomach, a relatively minimal amount in the small intestine and reportedly about 85% or more in the large intestine. Such a dosage form provides for a widely varying time-release of drug after administration that may not begin for 1–3 hours until the dosage form has passed from the stomach and an additional 3 hours or more for the dosage form to pass into the large intestine. While nefazodone is described generally as being an example of drugs that may be included in the formulation, no particular description of a formulation containing nefazodone is provided; nor is a formulation described that would provide a release profile for nefazodone and related compounds that optimally would be one of sustained release such that after administration drug would be released at a uniform rate over time. Furthermore, the type of release profile described in the patent may be less than satisfactory for the administration of antidepressants.

U.S. Pat. No. 5,169,638 describes a buoyant controlled release pharmaceutical powder formulation to be filled into capsules that uses a pH dependent polymer formed from alginic acid and hydroxypropylmethyl cellulose to release pharmaceuticals at a controlled rate. It appears from the disclosure that the capsule formulation was intended to mimic the characteristics of a tableted formulation. While, nefazodone is disclosed generally as being deliverable in accordance with method of the description, as is the case with U.S. Pat. No. 5,536,507 discussed above, no description is provided of a formulation that provides the uniform release characteristics of the dosage forms containing nefazodone and related compounds of the present invention.

Devices in which a drug composition is delivered as a slurry, suspension or solution from a small exit orifice by the action of an expandable layer are described in U.S. Pat. Nos. 5,633,011; 5,190,765; 5,252,338; 5,620,705; 4,931,285; 5,006,346; 5,024,842; and 5,160,743, which are incorporated herein by reference. Typical devices include an expandable push layer and a drug layer surrounded by a semipermeable membrane. In certain instances, the drug layer is provided with a subcoat to delay release of the drug composition to the envirnoment of use or to form an annealed coating in conjunction with the semipermeable membrane.

Devices in which a drug composition is delivered in a dry state from a large exit orifice by the action of an expandable layer are described in U.S. Pat. Nos. 4,892,778, 4,915,949 and 4,940,465. Those references describe a dispenser for delivering a beneficial agent to an environment of use that includes a semipermeable wall containing a layer of expandable material that pushes a dry drug layer out of the compartment formed by the wall. The exit orifice in the device is substantially the same diameter as the inner diameter of the compartment formed by the wall.

U.S. Pat. No. 5,126,142, which is incorporated herein by reference, describes a device for delivering an ionophore to livestock that includes a semipermeable housing in which a composition containing the ionophore and a carrier and an expandable hydrophilic layer is located, along with an additional element that imparts sufficient density to the device to retain it in the rumen-reticular sac of a ruminant animal. The ionophore and carrier are present in a dry state during storage and the composition changes to a dispensable, fluid-like state when it is in contact with the fluid environment of use. A number of different exit arrangements are described, including a plurality of holes in the end of the device and a single exit of varying diameter to control the amount of drug released per unit time due to diffusion and osmotic pumping.

While dosage forms delivering the drug composition to the environment of use in the dry state may provide suitable release of drug over a prolonged period of time, the exposure of the drug layer to the environment of use may result in agitation-dependent release of drug that in some circumstances is difficult to control. Accordingly, it may be advantageous to release the drug as a slurry or suspension that may be metered by control of rate of expansion of the push layer and the size of the exit orifice in the dosage form as in accordance with this invention.

Although a variety of sustained release dosage forms for delivering certain drugs exhibiting short half-life may be known, not every drug may be suitably delivered from those dosage forms because of solubility, metabolic processes, absorption and other physical, chemical and physiological parameters that may be unique to the drug and the mode of delivery.

An aspect of delivery of the antidepressants described herein is that the administration of high dosages of drug may require drug loading in the compositions and dosage forms being administered in the range of 20% to 90% of the overall weight of the composition or dosage form. Such loading requirements may present problems in formulating compositions and fabricating dosage forms and devices that are suitable for oral administration and can be swallowed without undue difficulty. Loading requirements may present problems when formulating dosage forms that are to be administered a limited number of times per day, such as for once-a-day dosing, with a goal of uniform release of active agent over a prolonged period of time.

There remains a need for effective dosing methods, dosage forms and devices that will permit the controlled release of the aforementioned compounds over a prolonged period of time to reduce the amount of the active agent that the patient is exposed to at any particular time and to increase the time between dosing, preferably to obtain a once-a-day dosing regimen.

SUMMARY OF THE INVENTION

In one aspect, the invention comprises a sustained release dosage form adapted to deliver a suspension or slurry and release over a prolonged period of time at a uniform rate of release a compound of the following structural formula:

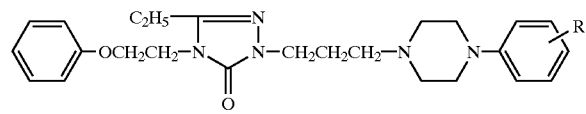

or a pharmaceutically acceptable acid addition salt thereof, wherein R is halogen. Preferably the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one or 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride and the prolonged period of time is six hours or greater.

In another aspect, the invention comprises a dosage form comprising a compound of the following structural formula:

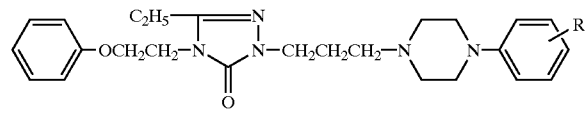

or a pharmaceutically acceptable acid addition salt thereof, wherein R is halogen, adapted to deliver a suspension or slurry of the compound and release the compound over a prolonged period of time at a uniform rate of release of at least 3 mg/hr. Preferably, the compound is nefazodone or nefazodone hydrochloride and the prolonged period of time is six hours or greater.

In yet another aspect, the invention comprises a method of treating a condition in a subject responsive to administration of a compound of the following structural formula:

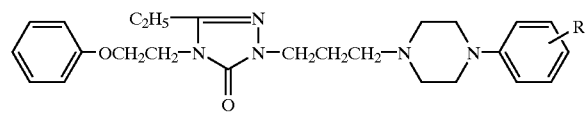

or a pharmaceutically acceptable acid addition salt thereof, wherein R is halogen, which comprises orally administering to the subject a dosage form adapted to release a suspension or a slurry of the compound at a uniform rate of release over a prolonged period of time. Preferably, the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one or 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride, and the dosage form comprises an osmotic material and between 50 and 1200 mg of the compound. Most preferably, the dosage form is administered orally, once-a-day.

In still another aspect, the invention comprises a dosage form comprising a wall defining a compartment, the wall having an exit orifice formed or formable therein and at least a portion of the wall being semipermeable; an expandable layer located within the compartment remote from the exit orifice and in fluid communication with the semipermeable portion of the wall; and a drug layer located within the compartment adjacent the exit orifice, the drug layer comprising a compound of the following structural formula:

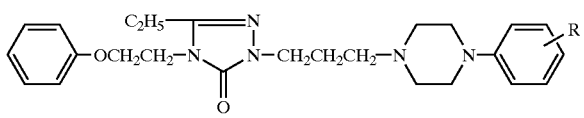

or a pharmaceutically acceptable acid addition salt thereof, wherein R is halogen, wherein the drug layer is adapted to form a suspension or a slurry of the compound in the environment of use. Preferably the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one or 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride. The dosage form may optionally comprise a flow-promoting layer between the wall and the drug layer.

In another aspect, the invention comprises a method of treating a condition responsive to administration of a compound having the following structural formula:

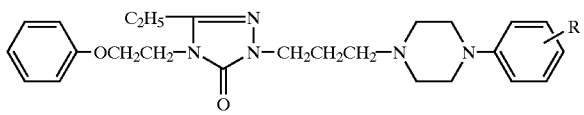

or a pharmaceutically acceptable acid addition salt thereof, wherein R is halogen, which comprises administering a slurry or suspension of the compound to provide a steady state plasma concentration of the compound of between 5 ng/ml and 2500 ng/ml with the proviso that during the 24 hour period after administration of the dosage form the quotient formed by $[C_{max} - C_{min}]/C_{min}$ is 3 or less. Preferably the compound is 2-[3-[4(3-chlorophenyl)-piperazinyl]propyl]-5-ethyl-4-(2-phenoxyethyl)-2$\underline{H}$-1,2,4-triazol-3(4$\underline{H}$)-one or 2-[3-[4(3-chlorophenyl)-piperazinyl]propyl]-5-ethyl-4-(2-phenoxyethyl)-2$\underline{H}$-1,2,4-triazol-3(4$\underline{H}$)-one hydrochloride.

DETAILED DESCRIPTION OF THE INVENTION

Figure 1A:
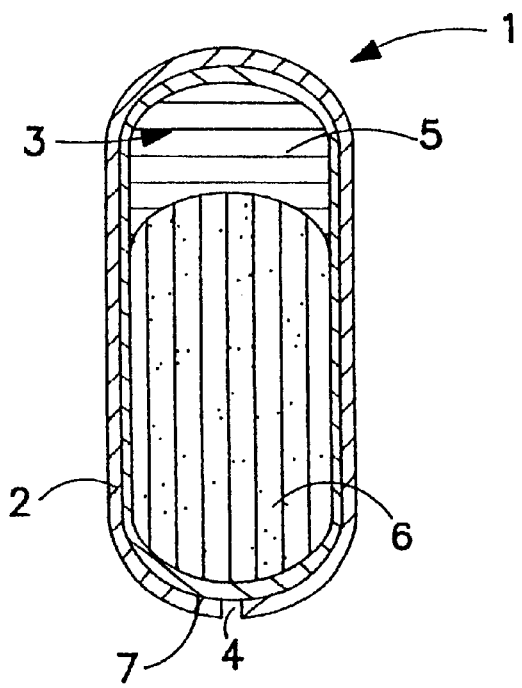
FIGS. 1A and 1B illustrate one embodiment of a dosage form of this invention, FIG. 1A illustrating the dosage form prior to administration to a subject and FIG. 1B illustrating the dosage form at a period of time after administration to a subject.

The present invention is best understood by reference to the following definitions, the drawings and exemplary disclosure provided herein.

Definitions

By "uniform rate of release" or "uniform release rate" is meant a rate of release of the active agent from a dosage form that does not vary positively or negatively by more than 30% from the mean rate of release of the active agent over a prolonged period of time, as determined in a USP Type 7 Interval Release Apparatus. Preferred uniform rates of release will vary by not more than 25% (positively or negatively) from the mean rate of release determined over a prolonged period of time.

By "prolonged period of time" or "prolonged period" is meant a continuous period of time of 4 hours or more, more typically 6 hours or more.

By "dosage form" is meant a pharmaceutical composition or device comprising an active pharmaceutical agent, the composition or device optionally containing inactive ingredients, such as pharmaceutically-acceptable carriers, excipients, suspension agents, surfactants, disintegrants, binders, diluents, lubricants, stabilizers, antioxidants, osmotic agents, colorants, plasticizers, and the like, that are used to manufacture and deliver active pharmaceutical agents.

By "active agent", "drug", or "compound" is meant an agent, drug, or compound having the following structural formula

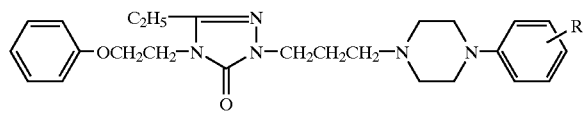

(Formula I)

or a pharmaceutically-acceptable acid addition salt thereof, wherein R is halogen.

By "halogen" is meant fluorine, iodine, chlorine and bromine. Chlorine and bromine are preferred halogens.

By "pharmaceutically-acceptable acid addition salt" or "pharmaceutically acceptable salt", which are used interchangeably herein, are meant those salts in which the anion does not contribute significantly to the toxicity or pharmacological activity of the salt, and, as such, they are the pharmacological equivalents of the bases of the compounds of Formula I. They are described in U.S. Pat. No. 4,338,317, which is incorporated by reference herein. Examples of pharmaceutically acceptable acids that are useful for the purposes of salt formation include but are not limited to hydrochloric, hydrobromic, hydroiodic, citric, acetic, benzoic, mandelic, phosphoric, nitric, mucic, isethionic, palmitic, and others.

By "sustained release" is meant continuous release of active agent to an environment over a prolonged period.

By "steady state" is meant the condition in which the amount of drug present in the blood plasma of a subject does not vary significantly over a prolonged period of time.

By "release rate assay" is meant a standardized assay for the determination of a compound using a USP Type 7 interval release apparatus substantially in accordance with the description of Example 2. It is understood that reagents of equivalent grade may be substituted in the assay in accordance with generally-accepted procedures.

By "C" is meant the concentration of drug in the blood plasma of a subject, generally expressed as mass per unit volume, typically nanograms per milliliter.

By "$C_{max}$" is meant the maximum concentration of drug in the blood plasma of a subject, generally expressed as mass per unit volume, typically nanograms per milliliter, within a specified time interval after administration of the drug to a subject.

By "$C_{min}$" is meant the minimum concentration of drug in the blood plasma of a subject, generally expressed as mass per unit volume, typically nanograms per milliliter, within a specified time interval after administration of the drug to a subject.

By "suspension" or "slurry" is meant active agent dissolved in, suspended in or in flowable admixture with a liquid. The liquid typically is aqueous, as existing in the gastric environment or as the bath of a release rate assay.

BRIEF DESCRIPTION OF THE DRAWINGS

Figure 1B:
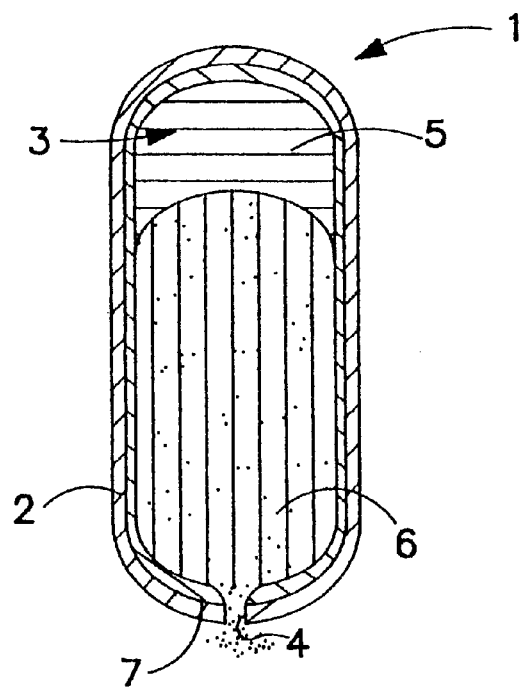

With reference to FIGS. 1A and 1B, a preferred embodiment of a dosage form of this invention is illustrated. The dosage form 1 comprises a wall 2 defining a compartment 3. Wall 2 is provided with an exit orifice 4. Within compartment 3 and remote from the exit orifice 4 is a push layer 5. A drug layer 6 is located within compartment 3 adjacent exit orifice 4. An optional secondary wall 7, the function of which will be described, may extend between drug layer 6 and the inner surface of wall 2. Secondary wall 7 may also extend between both drug layer 6 and push layer 5 and the inner surface of wall 2.

Wall 2 is formed to be permeable to the passage of an external fluid, such as water and biological fluids, and it is substantially impermeable to the passage of active agent, osmagent, osmopolymer and the like. As such, it is semipermeable. The selectively semipermeable compositions used for forming the wall are essentially nonerodible and they are insoluble in biological fluids during the life of the dosage form.

Representative polymers for forming wall 2 comprise semipermeable homopolymers, semipermeable copolymers, and the like. Such materials comprise cellulose esters, cellulose ethers and cellulose ester-ethers. The cellulosic polymers have a degree of substitution (DS) of their anhydroglucose unit of from greater than 0 up to 3, inclusive. Degree of substitution (DS) means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like, wherein the organic moieties contain from one to twelve carbon atoms, and preferably from one to eight carbon atoms.

The semipermeable compositions typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%; cellulose diacetate having a DS of 1 to 2 and an acetyl content of 21 to 35%; cellulose triacetate having a DS of 2 to 3 and an acetyl content of 34 to 44.8%; and the like. More specific cellulosic polymers include cellulose propionate having a DS of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45%, and a hydroxyl content of 2.8 to 5.4%; cellulose acetate butyrate having a DS of 1.8, an acetyl content of 13 to 15%, and a butyryl content of 34 to 39%; cellulose acetate butyrate having an acetyl content of 2 to 29%, a butyryl content of 17 to 53%, and a hydroxyl content of 0.5 to 4.7%; cellulose triacylates having a DS of 2.6 to 3, such as cellulose trivalerate, cellulose trilamate, cellulose tripalmitate, cellulose trioctanoate and cellulose tripropionate; cellulose diesters having a DS of 2.2 to 2.6, such as cellulose disuccinate, cellulose dipalmitate, cellulose dioctanoate, cellulose dicaprylate, and the like; and mixed cellulose esters, such as cellulose acetate valerate, cellulose acetate succinate, cellulose propionate succinate, cellulose acetate octanoate, cellulose valerate palmitate, cellulose acetate heptanoate, and the like. Semipermeable polymers are known in U.S. Pat. No. 4,077,407, and they can be synthesized by procedures described in *Encyclopedia of Polymer Science and Technology*, Vol. 3, pp. 325–354 (1964), Interscience Publishers Inc., New York, N.Y.

Additional semipermeable polymers for forming the outer wall 2 comprise cellulose acetaldehyde dimethyl acetate; cellulose acetate ethylcarbamate; cellulose acetate methyl carbamate; cellulose dimethylaminoacetate; semipermeable polyamide; semipermeable polyurethanes; semipermeable sulfonated polystyrenes; cross-linked selectively semipermeable polymers formed by the coprecipitation of an anion and a cation, as disclosed in U.S. Pat. Nos. 3,173,876; 3,276,586; 3,541,005; 3,541,006 and 3,546,142; semipermeable polymers, as disclosed by Loeb, et al. in U.S. Pat. No. 3,133,132; semipermeable polystyrene derivatives; semipermeable poly(sodium styrenesulfonate); semipermeable poly(vinylbenzyltrimethylammonium chloride); and semipermeable polymers exhibiting a fluid permeability of $10^{-5}$ to $10^{-2}$ (cc. mil/cm hr.atm), expressed as per atmosphere of hydrostatic or osmotic pressure differences across a semipermeable wall. The polymers are known to the art in U.S. Pat. Nos. 3,845,770; 3,916,899 and 4,160,020; and in *Handbook of Common Polymers*, Scott and Roff (1971) CRC Press, Cleveland, Ohio.

Wall 2 also can comprise a flux regulating agent. The flux regulating agent is a compound added to assist in regulating the fluid permeability or flux through wall 2. The flux regulating agent can be a flux enhancing agent or a decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, poilyalkylenediols, polyesters of alkylene glycols, and the like. Typical flux enhancers include polyethylene glycol 300, 400, 600, 1500, 4000, 6000 and the like; low molecular weight gylcols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; esters such as ethylene glycol dipropionate, ethylene glycol butyrate, butylene glucol dipropionate, glycerol acetate esters, and the like. Representative flux decreasing agents include phthalates substituted with an alkyl or alkoxy or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterfied with long chain alkyl groups; inert and substantially water impermeable fillers; resins compatible with cellulose based wall forming materials, and the like.

Other materials that can be used to form the wall 2 for imparting flexibility and elongation properties to the wall, for making wall 2 less-to-nonbrittle and to render tear strength, include phthalate plasticizers such as dibenzyl phthalate, dihexyl phthalate, butyl octyl phthalate, straight chain phthalates of six to eleven carbons, di-isononyl phthalte, di-isodecyl phthalate, and the like. The plasticizers include nonphthalates such as triacetin, dioctyl azelate, epoxidized tallate, tri-isoctyl trimellitate, tri-isononyl trimellitate, sucrose acetate isobutyrate, epoxidized soybean oil, and the like. The amount of plasticizer in a wall when incorporated therein is about 0.01% to 20% weight, or higher.

The drug layer 6 comprises a composition formed of a compound and a carrier, such as a hydrophilic polymer, that imbibes water to form a slurry or suspension of the compound within the compartment 3 formed by wall 2. The hydrophilic polymer provides a hydrophilic polymer particle in the drug composition that contributes to the uniform release rate of active agent and controlled delivery pattern. Representative examples of these polymers are poly (alkylene oxide) of 100,000 to 750,000 number-average molecular weight, including poly(ethylene oxide), poly (methylene oxide), poly(butylene oxide) and poly(hexylene oxide); and a poly(carboxymethylcellulose) of 40,000 to 400,000 number-average molecular weight, represented by poly(alkali carboxymethylcellulose), poly(sodium carboxymethylcellulose), poly(potassium carboxymethylcellulose) and poly(lithium carboxymethylcellulose). The drug composition can comprise a hydroxypropylalkylcellulose of 9,200 to 125,000 number-average molecular weight for enhancing the delivery properties of the dosage form as represented by hydroxypropylethylcellulose, hydroxypropyl methylcellulose, hydroxypropylbutylcellulose and hydroxypropylpentylcellulose; and a poly(vinylpyrrolidone) of 7,000 to 75,000 number-average molecular weight for enhancing the flow properties of the dosage form. Preferred among those polymers are the poly(ethylene oxide) of 100,000–300,000 number average molecular weight. Carriers that erode in the gastric environment, i.e., bioerodible carriers, are especially preferred.

Surfactants and disintegrants may be utilized in the carrier as well. Exemplary of the surfactants are those having an HLB value of between about 10–25, such as polyethylene glycol 400 monostearate, polyoxyethylene-4-sorbitan monolaurate, polyoxyethylene-20-sorbitan monooleate, polyoxyethylene-20-sorbitan monopalmitate, polyoxyethylene-20-monolaurate, polyoxyethylene-40-stearate, sodium oleate and the like. Disintegrants may be selected from starches, clays, celluloses, algins and gums and crosslinked starches, celluloses and polymers. Representative disintegrants include corn starch, potato starch, croscarmelose, crospovidone, sodium starch glycolate, Veegum HV, methylcellulose, agar, bentonite, carboxymethylcellulose, alginic acid, guar gum and the like.

The drug layer 6 is formed as a mixture containing compound and the carrier that when contacted with biological fluids in the environment of use provides a slurry or suspension of the compound that may be dispensed by the action of the expandable layer. The drug layer may be formed from particles by comminution that produces the size of the drug and the size of the accompanying polymer used in the fabrication of the drug layer, typically as a core containing the compound, according to the mode and the manner of the invention. The means for producing particles include granulation, spray drying, sieving, lyophilization, crushing, grinding, jet milling, micronizing and chopping to produce the intended micron particle size. The process can be performed by size reduction equipment, such as a micropulverizer mill, a fluid energy grinding mill, a grinding mill, a roller mill, a hammer mill, an attrition mill, a chaser mill, a ball mill, a vibrating ball mill, an impact pulverizer mill, a centrifugal pulverizer, a coarse crusher and a fine crusher. The size of the particle can be ascertained by screening, including a grizzly screen, a flat screen, a vibrating screen, a revolving screen, a shaking screen, an oscillating screen and a reciprocating screen. The processes and equipment for preparing drug and carrier particles are disclosed in *Pharmaceutical Sciences*, Remington, 17th Ed., pp. 1585–1594 (1985); *Chemical Engineers Handbook*, Perry, 6th Ed., pp. 21–13 to 21–19 (1984); *Journal of Pharmaceutical Sciences*, Parrot, Vol. 61, No. 6, pp. 813–829 (1974); and *Chemical Engineer*, Hixon, pp. 94–103 (1990).

The active compound may be provided in the drug layer in amounts of from 10 mg to 1200 mg per dosage form, depending upon the required dosing level that must be maintained over the delivery period, i.e., the time between consecutive administrations of the dosage forms. More typically, loading of compound in the dosage forms will provide doses of compound to the subject ranging from 10–600 mg per day, more usually 100 mg to 600 mg per day. Generally, if a total drug dose of more than 600 mg per day is required, multiple units of the dosage form may be administered at the same time to provide the required amount of drug. The drug layer initially will be a dry composition formed by compression of the carrier and the drug as one layer and the expandable or push layer as the second layer. The expandable layer will push the drug layer from the exit orifice as the push layer imbibes fluid from the environment of use, and the drug layer will take up fluid from the gastric environment to provide a slurry or suspension of the compound to be dispensed from the dosage form into the environment of use.

As a representative compound of the compounds having antidepressant activity described herein, immediate release nefazodone hydrochloride is typically administered at a starting dose of 200 mg/day, administered in two divided doses (BID). The effective dose range has been determined to be generally 300 mg/day to 600 mg/day. Observation of tolerability and need for additional clinical effect over the starting dose often results in the dose being increased in increments of 100 mg/day to 200 mg/day, on a BID schedule, at intervals of no less than one week. Several weeks of treatment often are required to obtain the full antidepressant response. Concurrently with observation, plasma concentrations in a subject may be determined by clinical assay to determine a correlation between tolerability and clinical effect and blood plasma concentrations of drug. Plasma concentrations may range from 5 to 2500 ng/ml (nanograms per milliliter), more typically 25 to 1500 ng/ml, of compound.

Comparable standards of observation of tolerability and clinical effect and clinical assays for blood plasma concentration that have been employed with immediate release dosage forms of the compounds may be employed to adjust the daily dose of the active agent in the sustained release dosage forms of this invention that are most appropriate for a particular subject. Generally, the lowest dose of compound providing the desired clinical effect will be utilized. Such dosages may be in the range of 10 mg/day to 1200 mg/day, more often in the range of 50 mg/day to 800 mg/day, and most often in the range of 100 mg/day to 600 mg/day, delivered to the subject over a prolonged period of time. Preferably the dose will be selected to provide a daily dose in the range of 50 mg/day to 800 mg/day, and most preferably from 100 mg/day to 600 mg/day.

Dosage forms of the present invention which provide a uniform release rate of the active compound may in appropriate circumstances allow one to use a lesser amount of compound per dosage form per day than would be calculated from simply multiplying the dose of active agent in the immediate release product by the number of times it is recommended to administer the immediate release product in a day. In other circumstances, an equal or greater daily dosage of the active agent may be required to elicit a desired patient response.

Even at high dosage levels in which the active compound is present from 40% to 90% by weight of the drug layer composition, the instant dosage forms and devices are able to effectively release the required amount of active compound over a prolonged period of time at a uniform release rate. Preferably, the weight percent of active compound in the dosage forms of the invention will be 75% or less, and most preferably less than 70%, but greater than 40%, most preferably about 50%, based on the weight of drug layer composition, to allow for dosage forms that may be easily swallowed. In circumstances where it is desirable to administer an amount of drug that would exceed 75% of the drug layer composition, it is usually preferred to simultaneously administer two tablets or more of the dosage form with a total drug loading equal to the greater amount that would have been used in the single tablet.

It has been found convenient for nefazodone and nefazodone hydrochloride, for example, to prepare once-a-day dosage forms in accordance with this invention having 100 mg, 200 mg, 300 mg, 400 mg and 500 mg of nefazodone hydrochloride per dosage form. After an initial start-up period, usually approximately 2–3 hours or less, the dosage forms provide a uniform rate of release of compound over a prolonged period of time, typically 4 hours to 20 hours or more, often for 4 hours to 16 hours, and more usually for a time period of 4 hours to 10 hours. At the end of a prolonged period of uniform release, the rate of release of drug from the dosage form may decline somewhat over a period of time, such as several hours. The dosage forms provide therapeutically effective amounts of drug for a broad range of applications and individual subject needs. Upon initial administration, the dosage forms may provide a drug concentration in the plasma of the subject that increases over an initial period of time, typically several hours or less, and then provide a relatively constant concentration of drug in the plasma over a prolonged period of time, typically 4 hours to 24 hours or more. The release profiles of the dosage forms of this invention provide release of drug over the entire 24-hour period corresponding to once-a-day administration, such that steady state concentration of drug in blood plasma of a subject may be maintained at therapeutically effective levels over a 24 hour period after administration of the sustained release dosage form. Steady state plasma levels of drug may typically be achieved after twenty-four hours or, in some cases, several days, e.g., 2–5 days, in most subjects.

Figure 2:
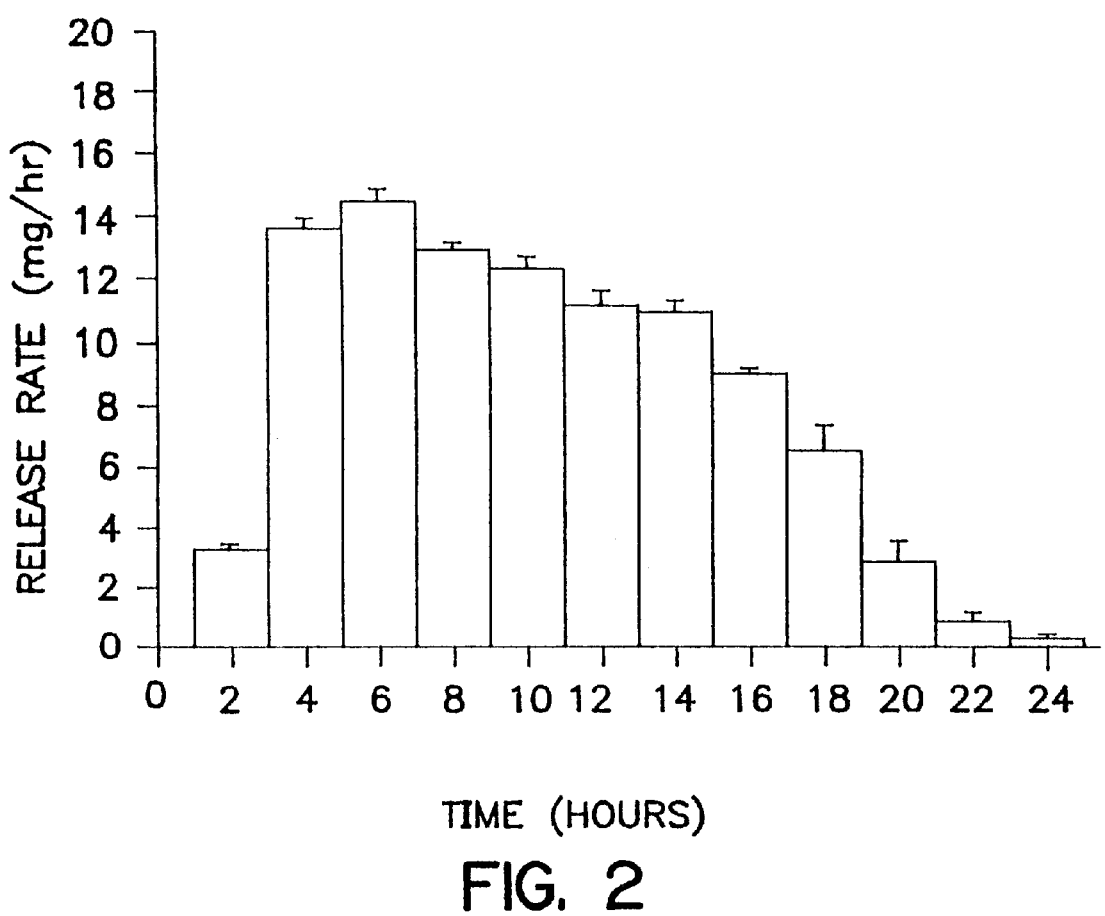
FIG. 2 illustrates a release profile (release rate as a function of time) of the active agent nefazodone hydrochloride from a representative dosage form having the general characteristics illustrated in FIG. 1, formed with an orifice of 50 mils and containing 200 mg of nefazodone hydrochloride.

Release rate as a function of time for a representative dosage form containing 200 mg of nefazodone hydrochloride is illustrated in FIG. 2. The dosage form had an average release rate of about 12.8 mg/hr over a period of about 12 hours. The dosage form was fabricated with an exit orifice of 50 mils, a 12.8 mg subcoat formed of 70/30 wt % Klucel/PVPK29-32 and a semipermeable membrane coat weighing 63.1 mg of 90/10 wt % cellulose acetate 398 and polyethylene glycol 3350.

The push layer 5 is an expandable layer comprising a push-displacement composition in contacting layered arrangement with the drug layer 6. It comprises a polymer that imbibes an aqueous or biological fluid and swells to push the drug composition through the exit means of the device. Representatives of fluid-imbibing displacement polymers comprise members selected from poly(alkylene oxide) of 1 million to 15 million number-average molecular weight, as represented by poly(ethylene oxide), and poly(alkali carboxymethylcellulose) of 500,000 to 3,500,000 number-average molecular weight, wherein the alkali is sodium, potassium or lithium. Examples of additional polymers for the formulation of the push-displacement composition comprise osmopolymers comprising polymers that form hydrogels, such as Carbopol® acidic carboxypolymer, a polymer of acrylic cross-linked with a polyallyl sucrose, also known as carboxypolymethylene, and carboxyvinyl polymer having a molecular weight of 250,000 to 4,000,000; Cyanamer® polyacrylamides; cross-linked water swellable indenemaleic anhydride polymers; Good-rite® polyacrylic acid having a molecular weight of 80,000 to 200,000; Aqua-Keeps® acrylate polymer polysaccharides composed of condensed glucose units, such as diester cross-linked polygluran; and the like. Representative polymers that form hydrogels are known to the prior art in U.S. Pat. No. 3,865,108, issued to Hartop; U.S. Pat. No. 4,002,173, issued to Manning; U.S. Pat. No. 4,207,893, issued to Michaels; and in *Handbook of Common Polymers*, Scott and Roff, Chemical Rubber Co., Cleveland, Ohio.

The osmagent, also known as osmotic solute and osmotically effective agent, which exhibits an osmotic pressure gradient across the outer wall and subcoat, comprises a member selected from the group consisting of sodium chloride, potassium chloride, lithium chloride, magnesium sulfate, magnesium chloride, potassium sulfate, sodium sulfate, lithium sulfate, potassium acid phosphate, mannitol, urea, inositol, magnesium succinate, tartaric acid raffinose, sucrose, glucose, lactose, sorbitol, inorganic salts, organic salts and carbohydrates.

Exemplary solvents suitable for manufacturing the hydro-activated layer and the wall comprise aqueous solvents and inert organic solvents that do not adversely harm the materials used in the system. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride nitroethane, nitropropane tetrachloroethane, ethyl ether, isopropyl ether, cyclohexane, cyclooctane, benzene, toluene, naphtha, 1,4-dioxane, tetrahydrofuran, diglyme, water, aqueous solvents containing inorganic salts such as sodium chloride, calcium chloride, and the like, and mixtures thereof such as acetone and water, acetone and methanol, acetone and ethyl alcohol, methylene dichloride and methanol, and ethylene dichloride and methanol.

The dosage form may comprise a device adapted to form a slurry or suspension of the compound comprising (1) a semipermeable wall that forms a compartment; (2) a drug composition in the compartment; (3) an exit orifice in the semipermeable wall; and optionally, (4) a secondary wall between at least the drug composition and the semipermeable wall that reduces friction between the external surface of the drug layer 6 and the inner surface of wall 2, promotes release of the drug composition from the compartment and reduces the amount of drug composition remaining in the compartment at the end of the delivery period, particularly when the slurry, suspension or solution of the drug composition that is being dispensed is highly viscous during the period of time in which it is being dispensed.

The optional secondary wall 7 is in contacting position with the inner surface of the semipermeable wall 2 and at least the external surface of the drug layer; although the secondary wall 7 may extend to and contact the external surface of the push layer. Optional secondary wall 7 may be formed as a coating applied over the compressed core comprising the drug layer and the push layer. The outer semipermeable wall 2 surrounds and encases the inner, secondary wall 7. Secondary wall 7 is preferably formed as a subcoat of at least the surface of the drug layer 6, and optionally the entire external surface of the compacted drug layer 6 and the push layer 5. When the semipermeable wall 2 is formed as a coat of the composite formed from the drug layer 6, the push layer 5 and the secondary wall 7, contact of the semipermeable wall 2 with the inner coat is assured.

Secondary wall 7 facilitates release of drug from the dosage forms of the invention. In dosage forms in which there is high drug loading, i.e., 40% or greater active agent in the drug layer based on the overall weight of the drug layer, and no secondary wall, it has been observed that significant residual amounts of drug may remain in the device after the period of delivery has been completed. In some instances, amounts of 20% or greater may remain in the dosage form at the end of a twenty-four hour period when tested in a release rate assay.

The amount of residual drug may be reduced by the addition of secondary wall 7 formed as an inner coat of a flow-promoting agent, i.e., an agent that lowers the frictional force between the outer, semi-permeable membrane wall 2 and the external surface of the drug layer 6. The secondary wall or inner coat 7 apparently reduces the frictional forces between the semipermeable wall 2 and the outer surface of the drug layer, thus allowing for more complete delivery of drug from the device. Particularly in the case of active compounds having a high cost, such an improvement presents substantial economic advantages since it is not necessary to load the drug layer with an excess of drug to insure that the minimal amount of drug required will be delivered.

The inner subcoat typically may be 0.01 to 5 mm thick, more typically 0.5 to 5 mm thick, and it comprises a member selected from hydrogels, gelatin, low molecular weight polyethylene oxides, e.g., less than 100,000 MW, hydroxyalkylcelluloses, e.g., hydroxyethylcellulose, hydroxypropylcellulose, hydroxyisopropylcelluose, hydroxybutylcellulose and hydroxyphenylcellulose, and hydroxyalkyl alkylcellulases, e.g., hydroxypropyl methylcellulose, and mixtures thereof. The hydroxyalkylcelluloses comprise polymers having a 9,500 to 1,250,000 number-average molecular weight. For example, hydroxypropyl celluloses having number average molecular weights of between 80,000 to 850,000 are useful. The flow promoting layer may be prepared from conventional solutions or suspensions of the aforementioned materials in aqueous solvents or inert organic solvents. Prefered materials for the subcoat or flow promoting layer include hydroxypropyl cellulose, hydroxyethyl cellulose, hydroxypropyl methyl cellulose, povidone [poly(vinylpyrrolidone)], polyethylene glycol, and mixtures thereof. More preferred are mixtures of hydroxypropyl cellulose and povidone, prepared in organic solvents, particularly organic polar solvents such as lower alkanols having 1–8 carbon atoms, preferably ethanol, mixtures of hydroxyethyl cellolose and hydroxypropyl methyl cellulose prepared in aqueous solution, and mixtures of hydroxyetyyl cellulose and polyethylene glycol prepared in aqueous solution. Most preferably, the subcoat consists of a mixture of hydroxypropyl cellulose and povidone prepared in ethanol. Conveniently, the weight of the subcoat applied to the bilayer core may be correlated with the thickness of the subcoat and residual drug remaining in a dosage form in a release rate assay such as described herein. During manufacturing operations, the thickness of the subcoat may be controlled by controlling the weight of the subcoat taken up in the coating operation.

When the secondary wall 7 is formed as a subcoat, i.e., by coating onto the tabletted bilayer composite drug layer and push layer, the subcoat can fill in surface irregularities formed on the bilayer core by the tabletting process. The resulting smooth external surface facilitates slippage between the coated bilayer composite and the semipermeable wall during dispensing of the drug, resulting in a lower amount of residual drug composition remaining in the device at the end of the dosing period. When wall 7 is fabricated of a gel-forming material, contact with water in the environment of use facilitates formation of the gel or gel-like inner coat having a viscosity that may promote and enhance slippage between outer wall 2 and drug layer 6.

Pan coating may be conveniently used to provide the completed dosage form, except for the exit orifice. In the pan coating system, the subcoat on the wall-forming compositions is deposited by successive spraying of the respective composition on the bilayered core comprising the drug layer and the push layer accompanied by tumbling in a rotating pan. A pan coater is used because of its availability at commercial scale. Other techniques can be used for coating the drug core. Finally, the wall or coated dosage form are dried in a forced-air oven, or in a temperature and humidity controlled oven to free the dosage form of solvent. Drying conditions will be conventionally chosen on the basis of available equipment, ambient conditions, solvents, coatings, coating thickness,and the like.

Other coating techniques can also be employed. For example, the semipermeable wall and the subcoat of the dosage form can be formed in one technique using the air-suspension procedure. This procedure consists of suspending and tumbling the bilayer core in a current of air, an inner subcoat composition and an outer semipermeable wall forming composition, until, in either operation, the subcoat and the outer wall coat is applied to the bilayer core. The air-suspension procedure is well suited for independently forming the wall of the dosage form. The air-suspension procedure is described in U.S. Pat. No. 2,799,241; in *J. Am. Pharm. Assoc.*, Vol. 48, pp. 451–459 (1959); and, ibid., Vol. 49, pp. 82–84 (1960). The dosage form also can be coated with a Wurster® air-suspension coater using, for example, methylene dichloride methanol as a cosolvent. An Aeromatic® air-suspension coater can be used employing a cosolvent.

The dosage form of the invention may be manufactured by standard techniques. For example, the dosage form may be manufactured by the wet granulation technique. In the wet granulation technique, the drug and the ingredients comprising the first layer or drug composition are blended using an organic solvent, such as denatured anhydrous ethanol, as the granulation fluid. The ingredients forming the first layer or drug composition are individually passed through a preselected screen and then thoroughly blended in a mixer. Next, other ingredients comprising the first layer can be dissolved in a portion of the granulation fluid, such as the solvent described above. Then, the latter prepared wet blend is slowly added to the drug blend with continual mixing in the blender. The granulating fluid is added until a wet blend is produced, which wet mass blend is then forced through a predetermined screen onto oven trays. The blend is dried for 18 to 24 hours at 24° C. to 35° C. in a forced-air oven. The dried granules are then sized. Next, magnesium stearate is added to the drug granulation, then put into milling jars and mixed on a jar mill for 10 minutes. The composition is pressed into a layer, for example, in a Manesty® press or a Korsch LCT press. The speed of the press is set at 20 rpm and the maximum load set at 2 tons. The first layer is pressed against the composition forming the second layer and the bilayer tablets are fed to a dry coater press, e.g., Kilian® Dry Coater press, and surrounded with the drug-free coat, followed by the exterior wall solvent coating.

In another manufacture the beneficial drug and other ingredients comprising the first layer facing the exit means are blended and pressed into a solid layer. The layer possesses dimensions that correspond to the internal dimensions of the area the layer is to occupy in the dosage form, and it also possesses dimensions corresponding to the second layer for forming a contacting arrangement therewith. The drug and other ingredients can also be blended with a solvent and mixed into a solid or semisolid form by conventional methods, such as ballmilling, calendering, stirring or rollmilling, and then pressed into a preselected shape. Next, a layer of osmopolymer composition is placed in contact with the layer of drug in a like manner. The layering of the drug formulation and the osmopolymer layer can be fabricated by conventional two-layer press techniques. The two contacted layers are first coated with a subcoat and an outer semipermeable wall. The air-suspension and air-tumbling procedures comprise in suspending and tumbling the pressed, contacting first and second layers in a current of air containing the delayed-forming composition until the first and second layers are surrounded by the wall composition.

Another manufacturing process that can be used for providing the compartment-forming composition comprises blending the powdered ingredients in a fluid bed granulator. After the powdered ingredients are dry blended in the granulator, a granulating fluid, for example, poly (vinylpyrrolidone) in water, is sprayed onto the powders.

The coated powders are then dried in the granulator. This process granulates all the ingredients present therein while adding the granulating fluid. After the granules are dried, a lubricant, such as stearic acid or magnesium stearate, is mixed into the granulation using a blender e.g., V-blender. The granules are then pressed in the manner described above.

The dosage form of the invention is provided with at least one exit orifice. The exit orifice cooperates with the drug core for the uniform release of drug from the dosage form. The exit orifice can be provided during the manufacture of the dosage form or during drug delivery by the dosage form in a fluid environment of use. The expression "exit orifice" as used for the purpose of this invention includes a member selected from the group consisting of a passageway; an aperture; an orifice; and a bore. The expression also includes an orifice that is formed from a substance or polymer that erodes, dissolves or is leached from the outer coat or wall or inner coat to form an exit orifice. The substance or polymer may include an erodible poly(glycolic) acid or poly(lactic) acid in the outer or inner coats; a gelatinous filament; a water-removable poly(vinyl alcohol); a leachable compound, such as a fluid removable pore-former selected from the group consisting of inorganic and organic salt, oxide and carbohydrate. An exit, or a plurality of exits, can be formed by leaching a member selected from the group consisting of sorbitol, lactose, fructose, glucose, mannose, galactose, talose, sodium chloride, potassium chloride, sodium citrate and mannitol to provide a uniform-release dimensioned pore-exit orifice. The exit orifice can have any shape, such as round, triangular, square, elliptical and the like for the uniform metered dose release of a drug from the dosage form. The dosage form can be constructed with one or more exits in spaced apart relation or one or more surfaces of the dosage form. The exit orifice can be performed by drilling, including mechanical and laser drilling, through the outer coat, the inner coat, or both. Exits and equipment for forming exits are disclosed in U.S. Pat. Nos. 3,845,770 and 3,916,899, by Theeuwes and Higuchi; in U.S. Pat. No. 4,063,064, by Saunders, et al.; and in U.S. Pat. No. 4,088,864, by Theeuwes, et al.

The dosage forms of the invention provide a therapeutic antidepressant effect when administered to subjects in need thereof. For most applications, dosage forms having 100–400 mg of drug per dosage form are convenient. In circumstance where there are higher dosing requirements, e.g., 500–1200 mg of drug per day, various combinations of the dosage forms containing lesser amounts of drug may be multiply dosed in combination at the same time to obtain similar delivery results as with dosage forms having higher drug loading.

With respect to the 100–400 mg dosage forms prepared as described herein, it has been found that, for a 100 mg dosage form having a core diameter of about 15/64 inch, an exit orifice of 30–60 mils, preferably 40–50 mils, and most preferably 50 mils, provides an effective release profile. For a 200 mg dosage form having a core diameter of about 17/64 inch, an exit orifice of 30–60 mils, preferably 40–50 mils, and most preferably 50 mils, provides an effective release profile. Comparable parameters may be selected for dosage forms having higher drug loading to give appropriate release profiles. Release rate profiles may be conveniently determined in a release rate assay, such as described herein, and correlated with clinical effect. The dosage forms release drug at a rate that varies less than 30% from the mean rate of release measured over a prolonged period of time. Preferably, the devices release drug at a rate that varies less than 25% from the mean rate of release measured over a prolonged period of time.

Dosage forms of this invention release drug as a suspension or a slurry at a uniform rate of release over a prolonged period of time as determined in a standard release rate assay such as that described herein. When administered to a subject, the dosage forms of the invention provide blood plasma levels of drug in the subject that are less variable over a prolonged period of time than those obtained with immediate release dosage forms. When the dosage forms of this invention are administered on a regular, once-a-day basis, the dosage forms of the invention provide steady state plasma levels of drug such that the difference between $C_{max}$ and $C_{min}$ over the 24-hour period is substantially reduced over that obtained from administration of an immediate release product that is intended to release the same amount of drug in the 24-hour period as is provided from the dosage forms of the invention.

The dosage forms of this invention are adapted to release active agent at a uniform rate of release rate over a prolonged period of time, preferably 6 hours or more. Measurements of release rate are typically made in vitro, in acidified water to provide a simulation of conditions in gastric fluid, and are made over finite, incremental time periods to provide an approximation of instantaneous release rate. Information of such in vitro release rates with respect to a particular dosage form may be used to assist in selection of dosage form that will provide desired in vivo results. Such results may be determined by present methods, such as blood plasma assays and clinical observation, utilized by practitioners for prescribing available immediate release dosage forms.

Dosage forms of this invention may provide blood plasma concentrations in the range of 5 to 2500 ng/ml, more typically in the range of 25 to 1200 ng/ml. Blood plasma of a subject to whom the dosage form has been administered may be assayed to determine the concentration of active agent in blood plasma as a function of time after the dosage form has been administered. This in effect allows for titration of the amount of drug to be administered to a subject over time. In order to obtain maximum concentrations of drug in blood plasma, it may be necessary to administer two or more dosage forms of the invention at the same time.

It has been found that dosage forms of the present invention having release rate profiles as defined herein will provide to a patient a substantially constant blood plasma concentration and a sustained therapeutic effect of active agent, after administration of the dosage form, over a prolonged period of time, notwithstanding the tendency of the active agents herein, i.e., the phenoxyethyl-substituted 1,2,4-triazol-3-ones, to be rapidity metabolized. The sustained release dosage forms of this invention demonstrate less variability in drug plasma concentration over a 24-hour period than do immediate release formulations, which characteristically create significant peaks in drug concentration shortly or soon after administration to the subject.

At steady state, the difference between $C_{max}$ and $C_{min}$ of drug in plasma of the subject to which the dosage form is administered over a 24-hour period after administration of a once-a-day dosage form is less than the difference between $C_{max}$ and $C_{min}$ for an immediate release dosage form(s) that is administered to provide the same total amount of drug over the period. While some subject-to-subject variability will be expected, the quotient formed from $[C_{max}-C_{min}]/C_{min}$ for a once-a-day dosage form may be on the order of 3 or less, often 2 or less, preferably 1 or less and most preferably ½ or less. For example, if at steady state $C_{max}$ is 200 ng/ml and $C_{min}$ is 100 ng/ml, the quotient will be 1. If $C_{max}$ is 200 and $C_{min}$ is 150, the quotient will be 1/3. If $C_{max}$ is 100 ng/ml and $C_{min}$ is 25 ng/ml, then the quotient is 1/3. Generally, the quotient determined from observed plasma concentrations can be expected to be larger with dosage forms containing lesser amounts of drug, although absolute variations in concentration may be smaller.

The invention comprises a method of treating disease states and conditions that are responsive to treatment with a compound of the following structural formula:

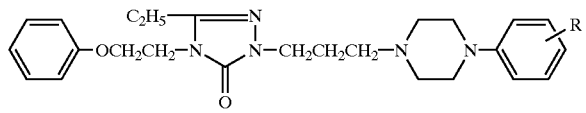

or its pharmaceutically acceptable salts, wherein R is halogen, by orally administering to a subject a dosage form adapted to release in a suspension or slurry the compound at a uniform rate of release over a prolonged period of time. Preferably the compound is nefazodone or nefazodone hydrochloride, and the release rate of the compound, as determined in a standard release rate assay, does not vary by more than 30% positively or negatively from the mean release rate over the prolonged period of time. In a most preferred embodiment, the release rate does not vary more than 25% positively or negatively from the mean release rate over the prolonged period of time. The method is practiced with dosage forms that are adapted to release the compound at uniform release rate of between 3 mg/hr to 60 mg/hr over a prolonged time period, preferably 6 hours or more, and most preferably 10 hours or more.

In another aspect, the method of treating disease states and conditions that are responsive to treatment with a compound of the following structural formula:

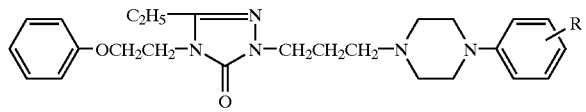

or its pharmaceutically acceptable salts, wherein R is halogen, comprises administering a slurry or suspension of the compound to a subject and maintaining over a prolonged period of time a steady state concentration of compound in the plasma of a subject between 5 ng/ml and 2500 ng/ml, wherein the difference between the maximum concentration of the compound in the plasma and the minimum concentration of the compound in the plasma during a prolonged period is 300% or less of the minimum concentration. That is, the quotient formed from $[C_{max}-C_{min}]/C_{min}$ is 3 or less. Preferably, the quotient is 2 or less, and most preferably 1 or less. The method wherein the quotient is ½ or less is especially preferred.

The practice of the foregoing methods by orally administering a dosage form of the invention to a subject once-a-day for the treatment of depression is preferred. Other disease states and conditions, which may be manifested or clinically diagnosed as symptoms of depression, may be treated with the dosage forms and methods of the invention.

A preferred method of manufacturing dosage forms of the present invention is generally described below. All percentages are weight percent unless otherwise noted.

EXAMPLE 1

Preparation of the Drug Layer Granulation

A binder solution is prepared by adding poly (vinylpyrrolidone), "PVP" [PVP K29-32], "HPC", to water to form a solution containing 8 g PVP per 100 grams of solution. The solution is mixed until the PVP is dissolved. For a desired batch size, a fluid bed granulator ("FBG") bowl is charged with the required amounts of nefazodone HCI (50%), polyethylene oxide (MW 200,000) (Polyox® N-80, Union Carbide Corporation) (44%), and PVP (5%). After mixing the dry materials in the bowl, the binder solution prepared as above is added. Then the granulation is dried in the FBG to a consistency suitable for milling (<1% by weight water), and the granulation is milled through a 7 or a 10 mesh screen.

The granulation is transferred to a tote or a V-blender. Antioxidant, butylated hydroxytoluene (BHT) (0.01%), and lubricant, stearic acid (0.99%), are sized through a 40 mesh screen and both are blended into the granulation using the tote or V-blender until uniformly dispersed (about 1 minute of blending for stearic acid and about 10 minutes of blending for BHT).

Preparation of the Osmotic Push Layer Granulation

A binder solution is prepared by adding hydroxypropyl methylcellulose 2910 ("HPMC") to water in a ratio of 5 mg of HPMC to 1 g of water. The solution is mixed until the HPMC is dissolved. Sodium chloride powder (30%) and red ferric oxide (1%) are milled and screened. A fluid bed granulator ("FBG") bowl is charged with the required amounts of polyethylene oxide (MW 7,000,000) (Polyox® 303) (63.7%), HPMC (5%), the sodium chloride and the red ferric oxide. After mixing the dry materials in the bowl, the binder solution prepared above is added. The granulation is dried in the FBG until the target moisture content (<1% by weight water) is reached. The granulation is milled through a 7 mesh screen and transferred to a tote or a V-blender. The required amount of antioxidant, butylated hydroxytoluene (0.08%), is sized through a 60 mesh screen. The required amount of lubricant, stearic acid (0.25%), is sized through a 40 mesh screen and both materials are blended into the granulation using the tote or blender until uniformly dispersed (about 1 minute for stearic acid and about 10 minutes for BHT).

Bilayer Core Compression

A longitudinal tablet press (Korsch press) is set up with round, deep concave punches and dies. Two feed hoppers are placed on the press. The drug layer prepared as above is placed in one of the hoppers while the osmotic push layer prepared as above is placed in the remaining hopper.

The initial adjustment of the tableting parameters (drug layer) is performed to produce cores with a uniform target drug layer weight in each tablet. The second layer adjustment (osmotic push layer) of the tableting parameters is performed which bonds the drug layer to the osmotic layer to produce cores with a uniform final core weight, thickness, hardness, and friability. The foregoing parameters can be adjusted by varying the fill space and/or the force setting.

Preparation of the Subcoat Solution and Subcoated System

The subcoat solution is prepared in a covered stainless steel vessel. The appropriate amounts of povidone (K29-32) (2.4%) and hydroxypropyl cellulose (MW 80,000) (Klucel EF, Aqualon Company) (5.6%) are mixed into anhydrous ethyl alcohol (92%) until the resulting solution is clear. The bilayer cores prepared above are placed into a rotating, perforated pan coating unit. The coater is started and after the coating temperature of 28–36° C. is attained, the subcoating solution prepared above is uniformly applied to the rotating tablet bed. When a sufficient amount of solution has been applied to provide the desired subcoat weight gain, the subcoat process is stopped. The desired subcoat weight will be selected to provide acceptable residuals of drug remaining in the dosage form as determined in the release rate assay for a 24-hour period. Generally, it is desirable to have less than 10%, more preferably less than 5%, and most preferably less than 3% of residual drug based on the initial drug loading. This may be determined from the correlation between subcoat weight and the residual drug for a number of dosage forms having the same bilayer core but different subcoat weights in the standard release rate assay.

Preparation of the Rate Controlling Membrane and Membrane Coated System

The subcoated bilayer cores prepared above are placed into a rotating, perforated pan coating unit. The coater is started, and after the coating temperature (28–38° C.) is attained, the coating solution is uniformly applied to the rotating tablet bed until the desired membrane weight gain is obtained. At regular intervals throughout the coating process, the weight gain is determined. Weight gain may be correlated with $T_{90}$ for membranes of varying thickness in the release rate assay. When sufficient amount of solution has been applied, conveniently determined by attainment of the desired membrane weight gain, the membrane coating process is stopped.

Drilling of Membrane Coated Systems

One exit port is drilled into the drug layer end of the membrane coated system. During the drilling process, samples are checked at regular intervals for orifice size, location, and number of exit ports. In a preferred embodiment, a target single orifice of 50 mils is drilled, on the drug layer end of the dosage form.

Drying of Drilled Coated Systems

Drilled coated systems prepared as above are placed on perforated oven trays which are placed on a rack in a relative humidity oven (43–45% relative humidity) and dried to remove the remaining solvents.

Color and Clear Overcoats

Optional color or clear coats solutions are prepared in a covered stainless steel vessel. For the color coat 88 parts of purified water is mixed with 12 parts of Opadry II [color not critical] until the solution is homogenous. For the clear coat 90 parts of purified water is mixed with 10 parts of Opadry Clear until the solution is homogeneous. The dried cores prepared as above are placed into a rotating, perforated pan coating unit. The coater is started and after the coating temperature is attained (35–45° C.), the color coat solution is uniformly applied to the rotating tablet bed. When sufficient amount of solution has been applied, as conveniently determined when the desired color overcoat weight gain has been achieved, the color coat process is stopped. Next, the clear coat solution is uniformly applied to the rotating tablet bed. When sufficient amount of solution has been applied, or the desired clear coat weight gain has been achieved, the clear coat process is stopped. A flow agent (e.g., Car-nu-bo wax) is applied to the tablet bed after clear coat application.

EXAMPLE 2

The release rate of drug from devices containing the dosage forms of the invention is determined in the following standardized assay. The method involves releasing systems into acidified water (pH 3). Aliquots of sample release rate solutions are injected onto a chromatographic system to quantify the amount of drug released during specified test intervals. Drug is resolved on a $C_{18}$ column and detected by UV absorption (254 nm for nefazodone hydrochloride). Quatitation is performed by linear regression analysis of peak areas from a standard curve containing at least five standard points.

Samples are prepared with the use of a USP Type 7 Interval Release Apparatus. Each system (invention device) to be tested is weighed. Then, each system is glued to a plastic rod having a sharpened end, and each rod is attached to a release rate dipper arm. Each release rate dipper arm is affixed to an up/down reciprocating shaker (USP Type 7 Interval Release Apparatus), operating at an amplitude of about 3 cm and 2 to 4 seconds per cycle. The rod ends with the attached systems are continually immersed in 50 ml calibrated test tubes containing 50 ml of acidified $H_2O$ (acidified to pH 3.00±0.05 with phosphoric acid), equilibrated in a constant temperature water bath controlled at 37° C.±0.5° C. At the end of each time interval specified, typically one hour or two hours, the systems are transferred to the next row of test tubes containing fresh acidified water. The process is repeated for the desired number of intervals until release is complete. Then the solution tubes containing released drug are removed and allowed to cool to room temperature. After cooling, each tube is filled to the 50 ml mark with acidified water, each of the solutions is mixed thoroughly, and then transferred to sample vials for analysis by high pressure liquid chromatography ("HPLC"). Standard solutions of drug are prepared in concentration increments encompassing the range of 5 micrograms to about 400 micrograms and analyzed by HPLC. A standard concentration curve is constructed using linear regression anaysis. Samples of drug obtained from the release test are analyzed by HPLC and concentration of drug is determined by linear regression analysis. The amount of drug released in each release interval is calculated. The results for a representative dosage form of the invention are illustrated in FIG. 2.

EXAMPLE 3

Employing the general procedure of EXAMPLE 1 and proportionate amounts of materials (all percentages expressed as weight percentages), a dosage form containing 200 mg of nefazadone hydrochloride is prepared.

For a unit dosage form, the drug layer having a weight of 400 mg consists of 50% nefazodone hydrochloride, 44% polyethylene oxide (Polyox N-80), 5% PVP K 29-32, 0.99% stearic acid and 0.01% butylated hydroxytoluene (BHT) is prepared. The push layer is prepared having a weight of 160 mg consisting of 63.67% polyethylene oxide (Polyox 303), 30.0% sodium chloride, 5% hydroxypropyl methylcellulose (HPMC E-5), 1% red ferric oxide, 0.25% stearic acid and 0.08% BHT. The bilayer core comprising the drug layer and the push layer is tablefted as described.

Next, a subcoat is prepared with 70% Klucel EF and 30% povidone K29-32 with ethanol as the solvent. The subcoat solution contains 8% solids on application. After application, the amount of the subcoat on the bilayer core is 12.8 mg. The semi-permeable membrane is prepared with 90% cellulose acetate 398-10 and 10% polyethylene glycol 3350 with a solvent system of 95% acetone and 5% methanol. The membrane coat solution contains 5% solids on application, and the weight of the membrane on the subcoated bilayer core after application is 63.1 mg.

An orifice having a diameter of 50 mils is drilled in the dosage forms, which are then dried at 45° C. and 45% relative humidity for about 120 hours and dried for an additional 5 hours at 45° C. at otherwise ambient conditions.

The dosage forms are assayed for release of nefazodone hydrochloride in the assay described in Example 2. The release rates for four individual dosage forms and the cumulative percent of dose released are represented in FIG. 2. The dosage forms exhibit a nominal $T_{90}$ of 16.2 hours and a mean release rate of 13.1 mg/hr over a prolonged period of time, extending substantially from interval 2 to interval 7. It is observed that the dosage forms release nefazodone hydrochloride at a uniform rate of release over a prolonged period of time.

EXAMPLE 4

Employing the general procedure of EXAMPLE 1 and proportionate amounts of materials (all percentages expressed as weight percentages), dosage forms containing 100, 300 and 400 mg nefazodone hydrochloride may be prepared. Those dosage forms release nefazodone hyddrochloride at a uniform rate of release over a prolonged period of time.

EXAMPLE 5

Representative samples of the dosage forms of this invention containing 100–400 mg of nefazodone hydrochloride having orifice diameters of about 50 mils are orally administered to subjects once-a-day. Blood samples are drawn from the subjects at regular intervals (typically 1–4 hours) and the blood plasma samples so obtained analyzed for amounts of nefazodone hydrochloride present. The dosage forms of the invention provide sustained blood plasma levels of between 5 ng/ml and 2500 ng/ml. Steady state blood plasma levels are maintained at uniformly therapeutic levels such that quotient that is formed from $[C_{max}-C_{min}]/C_{min}$ for nefazodone hydrochloride in plasma over the 24-hour interval after administration is 3 or less.

The invention comprises the following characteristics and features, either alone or in combination with one or more of each other:

A sustained release dosage form adapted to release as a suspension or a slurry over a prolonged period of time at a uniform rate of release a compound of the following structural formula: or a pharmaceutically acceptable acid addition salt thereof, wherein R is halogen; the dosage form wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one; the dosage form wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride; the dosage form wherein the prolonged period of time is six hours or greater; the dosage form wherein the prolonged period of time is eight hours or greater; the dosage form wherein the prolonged period of time is 10 hours or greater; the dosage form wherein the compound is released at a rate of at least 3 mg/hr; a composition comprising a compound of the following structural formula:

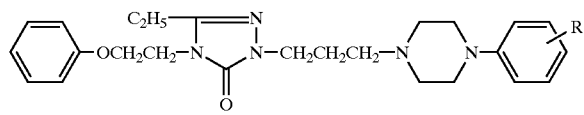

or a pharmaceutically acceptable acid addition salt thereof, wherein R is halogen, adapted to release as a suspension or a slurry the compound over a prolonged period of time at a uniform rate of release of at least 3 mg/hr; the composition wherein the compound is nefazodone or nefazodone hydrochloride; the composition wherein the prolonged period of time is six hours or greater; the composition wherein the uniform rate of release is not more than 60 mg/hr; a method of treating a condition in a subject responsive to administration of a compound of the following structural formula:

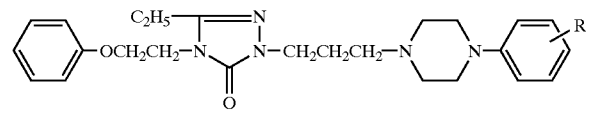

or a pharmaceutically acceptable acid addition salt thereof, wherein R is halogen, which comprises orally administering to the subject a dosage form adapted to release as a suspension or a slurry the compound at a uniform rate of release over a prolonged period of time; the method wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one; the method wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride; the method wherein the dosage form contains between 50 and 1200 mg of the compound; the method wherein the dosage form comprises an osmotic material; a dosage form adapted to release a suspension or a slurry of a compound of the following structural formula:

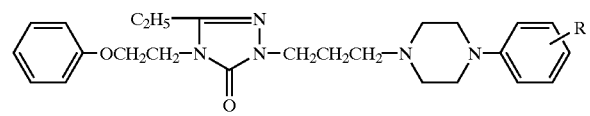

or a pharmaceutically acceptable acid addition salt thereof, wherein R is halogen, comprising: a wall defining a compartment, the wall having an exit orifice formed or formable therein and at least a portion of the wall being semipermeable, an expandable layer located within the compartment remote from the exit orifice and in fluid communication with the semipermeable portion of the wall, and a drug layer located within the compartment adjacent the exit orifice, the drug layer comprising a compound and a hydrophillic carrier; the dosage form wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one; the dosage form wherein the compound is 2-[3-[4-(3-chlorophenyl)-piperazinyl]propyl]-5-ethyl-4-(2-phenoxyethyl)-2$\underline{H}$-1,2,4-triazol-3(4$\underline{H}$)-one hydrochloride; the dosage form comprising a flow-promoting layer between the wall and the drug layer; a method of treating a condition responsive to administration of a compound having the following structural formula:

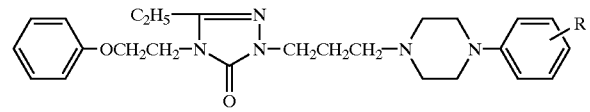

or a pharmaceutically acceptable acid addition salt thereof, wherein R is halogen, which comprises administering a suspension or a slurry of the compound to maintain over a prolonged period of time a steady state concentration of compound in the plasma of a subject between 5 ng/ml and 2500 ng/ml, wherein the quotient formed from $[C_{max}-C_{min}]/$ $C_{min}$ is 3 or less; the method wherein the compound is 2-[3-[4(3-chlorophenyl)-piperazinyl]propyl]-5-ethyl-4-(2-phenoxyethyl)-2H-1,2,4-triazol-3(4H)-one; the method wherein the compound is 2-[3-[4(3-chlorophenyl)-piperazinyl]propyl]-5-ethyl-4-(2-phenoxyethyl)-2H-1,2,4-triazol-3(4H)-one hydrochloride; the method wherein the quotient is 2 or less; and the method wherein the quotient is 1 or less.

The above-described exemplary embodiments are intended to be illustrative in all respects, rather than restrictive, of the present invention. Thus, the present invention is capable of implementation in many variations and modifications that can be derived from the description herein by a person skilled in the art. All such variations and modifications are considered to be within the scope and spirit of the present invention as defined by the following claims.

What is claimed is:

1. A sustained release osmotic dosage form without a delayed release coating adapted for once-a-day administration comprising a substantially dry core wherein the core is hydrated following administration to release as a suspension or a slurry over a prolonged period of time beginning 3 hours or less after administration at a uniform rate of release a compound of the following structural formula:

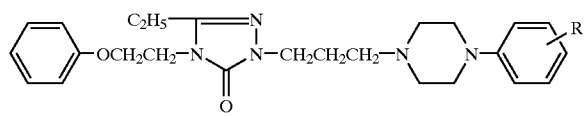

or a pharmaceutically acceptable acid addition salt thereof, wherein R is halogen.

2. The dosage form of claim 1 wherein the compound is 2-[3-[4-(3-chlorophenyl)-piperazinyl]propyl]-5-ethyl-4-(2-phenoxyethyl)-2H-1,2,4-triazol-3(4H)-one.

3. The dosage form of claim 1 wherein the compound is 2-[3-[4-(3-chlorophenyl)-piperazinyl]propyl]-5-ethyl-4-(2-phenoxyethyl)-2H-1,2,4-triazol-3(4H)-one hydrochloride.

4. The dosage form of claim 1 wherein the prolonged period of time is six hours or greater.

5. The dosage form of claim 1 wherein the prolonged period of time is eight hours or greater.

6. The dosage form of claim 1 wherein the prolonged period of time is 10 hours or greater.

7. The dosage form of claim 1 wherein the compound is released at a rate of at least 3 mg/hr.

8. The dosage form of claim 7 wherein the prolonged period of time is six hours or greater.

9. An osmotic composition comprising a compound of the following structural formula:

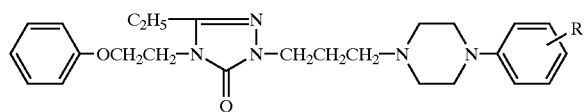

or a pharmaceutically acceptable acid addition salt thereof, wherein R is halogen, adapted for once-a-day administration without a delayed release coating comprising a substantially dry core wherein the core is hydrated following administration to release as a suspension or a slurry the compound over a prolonged period of time beginning 3 hours or less after administration at a uniform rate of release of at least 3 mg/hr.

10. The composition of claim 9 wherein the compound is nefazodone or nefazodone hydrochloride.

11. The composition of claim 10 wherein the prolonged period of time is six hours or greater.

12. The composition of claim 9 wherein the uniform rate of release is not more than 60 mg/hr.

13. A method of treating depression comprising once-a-day administration of a compound of the following structural formula:

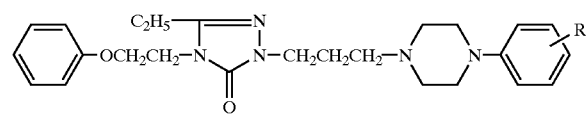

or a pharmaceutically acceptable acid addition salt thereof, wherein R is halogen, which comprises orally administering to the subject an osmotic dosage form comprising a substantially dry core wherein the core is hydrated following administration, adapted without a delayed release coating, to release as a suspension or a slurry the compound at a uniform rate of release over a prolonged period of time beginning 3 hours or less after administration.

14. The method of claim 13 wherein the compound is 2-[3-[4-(3-chlorophenyl)-piperazinyl]propyl]-5-ethyl-4-(2-phenoxyethyl)-2H-1,2,4-triazol-3(4H-one.

15. The method of claim 14 wherein the compound is 2-[3-[4-(3-chlorophenyl)-piperazinyl]propyl]-5-ethyl-4-(2-phenoxyethyl)-2H-1,2,4-triazol-3(4H)-one hydrochloride.

16. The method of claim 15 wherein the dosage form contains between 50 and 1200 mg of the compound.

17. The method of claim 16 wherein the dosage form comprises an osmotic material.

18. An osmotic dosage form adapted to release a suspension or a slurry of a compound of the following structural formula:

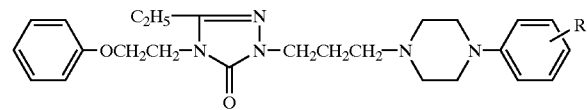

or a pharmaceutically acceptable acid addition salt thereof, wherein R is halogen, comprising: a wall defining a compartment, the wall having an exit orifice formed or formable therein and at least a portion of the wall being semipermeable; an expandable layer located within the compartment remote from the exit orifice and in fluid communication with the semipermeable portion of the wall; and a dried drug layer located within the compartment adjacent the exit orifice, the dried drug layer comprises the compound and a hydrophillic carrier wherein the dried drug layer hydrates after administration to form a slurry or suspension and the expandable layer expands to deliver the hydrated drug layer.

19. The dosage form of claim 18 wherein the compound is 2-[3-[4-(3-chlorophenyl)-piperazinyl]propyl]-5-ethyl-4-(2-phenoxyethyl)-2H-1,2,4-triazol-3(4H)-one.

20. The dosage form of claim 18 wherein the compound is 2-[3-[4-(3-chlorophenyl)-piperazinyl]propyl]-5-ethyl-4-(2-phenoxyethyl)-2H-1,2,4-triazol-3(4H)-one hydrochloride.

21. The dosage form of claim 18 comprising a flow-promoting layer between the wall and the drug layer.

22. A method of treating depression comprising once-a-day administration of a compound having the following structural formula:

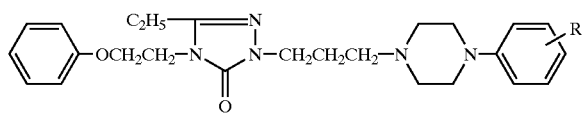

or a pharmaceutically acceptable acid addition salt thereof, wherein R is halogen, which comprises administering an osmotic dosage form comprising a substantially dry core wherein the core is hydrated following administration to release a suspension or a slurry of the compound to maintain over a prolonged period of time a steady state concentration of compound in the plasma of a subject between 5 ng/ml and 2500 ng/ml, wherein the quotient formed from $[C_{max}-C_{min}]/C_{min}$ is 3 or less.

23. The method of claim 22 wherein the compound is 2-[3-[4(3-chlorophenyl)-piperazinyl]propyl]-5-ethyl-4-(2-phenoxyethyl)-2$\underline{H}$-1,2,4-triazol-3(4$\underline{H}$)-one.

24. The method of claim 22 wherein the compound is 2-[3-[4(3-chlorophenyl)-piperazinyl]propyl]-5-ethyl-4-(2-phenoxyethyl)-2$\underline{H}$-1,2,4-triazol-3(4$\underline{H}$)-one hydrochloride.

25. The method of claim 22 wherein the quotient is 2 or less.

26. The method of claim 22 wherein the quotient is 1 or less.

* * * * *